(12) United States Patent
Kochura et al.

(10) Patent No.: US 10,790,055 B2
(45) Date of Patent: *Sep. 29, 2020

(54) APPETITE IMPROVEMENT SYSTEM THROUGH MEMORY ASSOCIATION

(71) Applicant: INTERNATIONAL BUSINESS MACHINES CORPORATION, Armonk, NY (US)

(72) Inventors: Nadiya Kochura, Bolton, MA (US); Fang Lu, Billerica, MA (US)

(73) Assignee: International Business Machines Corporation, Armonk, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/204,180

(22) Filed: Nov. 29, 2018

(65) Prior Publication Data
US 2019/0096519 A1     Mar. 28, 2019

Related U.S. Application Data

(63) Continuation of application No. 15/489,917, filed on Apr. 18, 2017.

(51) Int. Cl.
*G16H 20/60* (2018.01)
*G06Q 50/00* (2012.01)
(Continued)

(52) U.S. Cl.
CPC ......... *G16H 20/60* (2018.01); *G06F 19/3475* (2013.01); *G06N 20/00* (2019.01);
(Continued)

(58) Field of Classification Search
USPC .................. 705/2; 707/722, 734; 434/127
See application file for complete search history.

(56) References Cited

U.S. PATENT DOCUMENTS 6,015,792 A   1/2000 Kurtz
6,326,400 B1  12/2001 Edmundson
(Continued)

FOREIGN PATENT DOCUMENTS

EP    3321787 A1 *  5/2018  .......... G06F 3/0488
WO    2005037100 A1   4/2005
(Continued)

OTHER PUBLICATIONS

IP.com Prior Art Database Technical Disclosure ("System and method for assessing consumer interaction via pattern detection and prediction in social networks," IPCOM000247311D. Aug. 22, 2016) (Year: 2016).*

(Continued)

*Primary Examiner* — Lynda Jasmin
*Assistant Examiner* — Johnathan J Lindsey, III
(74) *Attorney, Agent, or Firm* — Rakesh Roy (57) ABSTRACT

Improving appetite through positive memory association. Information is received including text content related to a user. A positive user sentiment is defined using sentiment analysis. Text analysis is applied on the text content to identify a factor in the information that correlates with the positive user sentiment. The factor is ranked based on a strength of the correlation. Responsive to determining that the strength of the correlation is above a predefined threshold, the factor is stored as a positive token. A list of food recipes is accessed to identify a food recipe that incorporates the positive token. The food recipe is displayed to the user.

7 Claims, 6 Drawing Sheets

USER INFORMATION STORAGE 150

USER PROFILE 151 | SOCIAL MEDIA INFORMATION 152 | DATA EXCHANGE INFORMATION 153

HEALTH CONDITION AND LIFESTYLE INFORMATION 154 | EMOTIONAL FEEDBACK INFORMATION 155 | FOOD INTAKE INFORMATION 156

(51) Int. Cl.
*G06N 20/00* (2019.01)
*G16H 30/40* (2018.01)
*G16H 40/63* (2018.01)
*G16H 50/70* (2018.01)
*G16H 50/20* (2018.01)
*G16H 40/67* (2018.01)
*G16H 20/70* (2018.01)
*G16H 20/90* (2018.01)
*G06F 19/00* (2018.01)

(52) U.S. Cl.
CPC .............. *G06Q 50/01* (2013.01); *G16H 30/40* (2018.01); *G16H 40/63* (2018.01); *G16H 40/67* (2018.01); *G16H 50/20* (2018.01); *G16H 50/70* (2018.01)

(56) References Cited

U.S. PATENT DOCUMENTS

| | | | |
|---|---|---|---|
| 8,067,185 B2 | 11/2011 | Zoller | |
| 8,417,713 B1* | 4/2013 | Blair-Goldensohn | G06F 16/335 707/751 |
| 8,838,438 B2* | 9/2014 | Leary | G06F 40/253 704/9 |
| 8,838,516 B2* | 9/2014 | Kunjithapatham | G06F 16/9535 706/45 |
| 9,146,947 B2* | 9/2015 | Luk | G06Q 30/02 |
| 9,364,106 B1 | 6/2016 | Ortiz | |
| 9,824,152 B1* | 11/2017 | Feller | G06F 16/9535 |
| 2005/0244548 A1 | 11/2005 | Cheng | |
| 2009/0149721 A1 | 6/2009 | Yang | |
| 2010/0292998 A1* | 11/2010 | Bodlaender | G06Q 30/0603 705/2 |
| 2013/0216982 A1 | 8/2013 | Bennett | |
| 2014/0030380 A1 | 1/2014 | Kitajima | |
| 2014/0095479 A1* | 4/2014 | Chang | G06F 16/335 707/722 |
| 2014/0223462 A1* | 8/2014 | Aimone | H04N 21/4788 725/10 |
| 2015/0313496 A1* | 11/2015 | Connor | A61B 5/0478 600/301 |
| 2016/0232811 A9 | 8/2016 | Connor | |
| 2017/0193096 A1* | 7/2017 | Bhatt | G06F 16/335 |
| 2018/0032701 A1* | 2/2018 | Zatvan | G16H 10/20 |
| 2018/0075490 A1* | 3/2018 | Chintalapoodi | H04N 21/4668 |
| 2018/0114284 A1* | 4/2018 | Greenberger | G06Q 50/12 |
| 2018/0189593 A1* | 7/2018 | DeLuca | G06K 9/6263 |
| 2018/0300460 A1 | 10/2018 | Kochura et al. | |

FOREIGN PATENT DOCUMENTS

| | | | |
|---|---|---|---|
| WO | WO-2012177229 A1 * | 12/2012 | .............. G10L 15/26 |
| WO | 2014085910 A1 | 6/2014 | |

OTHER PUBLICATIONS

Chai M. Tyng et. al., "The Influences of Emotion on Learning and Memory," Front. Psychol. 8:1454 (Aug. 2017) (Year: 2017).*

IP.com Prior Art Database Technical Disclosure ("System and method for assessing consumer interaction via pattern detection and prediction in social networks," IPCOM000247311D. Aug. 22, 2016). (Year: 2016).*

Tyng (Chai M. Tyng et. al., "The Influences of Emotion on Learning and Memory," Front. Psychol. 8:1454 (Aug. 2017)). (Year: 2017).*

EIC 3600 Search Report dated Mar. 10, 2020 (Year: 2020).*

EIC 3600 Search Report dated May 8, 2020 (Year: 2020).*

IBM, List of IBM Patents or Patent Applications Treated as Related, Appendix P, dated Nov. 30, 2018, 2 pages.

Anonymous Inventors; Ttl: System and method for assessing consumer interaction via pattern detection and prediction in social networks; Aug. 22, 2016; Database: IP.com; IP.com No. IPCOM000247311D.

Baral, "Neurogastronomy 101: The Science of Taste Perception", Oct. 2015, pp. 1-8, EATER.com, Vox Media.

Mell et al., "The NIST Definition of Cloud Computing", NIST, Sep. 2011, pp. 1-3, Special Publication 800-145, U.S. Department of Commerce, Gaithersburg, MD.

Wikipedia, "Alpha Wave", Wikipedia, Printed on Apr. 14, 2017, pp. 1-5, United States.

* cited by examiner

APPETITE IMPROVEMENT SYSTEM THROUGH MEMORY ASSOCIATION

FIELD OF THE INVENTION

The present invention relates generally to the field of health and wellness improvement technologies, and more particularly improving a user's appetite through memory association.

SUMMARY

Embodiments of the present invention provide systems, methods, and computer program products for improving appetite through positive memory association. Information is received including text content related to a user. A positive user sentiment is defined using sentiment analysis. Text analysis is applied on the text content to identify a factor in the information that correlates with the positive user sentiment. The factor is ranked based on a strength of the correlation. Responsive to determining that the strength of the correlation is above a predefined threshold, the factor is stored as a positive token. A list of food recipes is accessed to identify a food recipe that incorporates the positive token. The food recipe is displayed to the user.

DETAILED DESCRIPTION

An individual may lose their appetite to eat food for a variety of reasons. For example, an individual may experience a reduced appetite if the weather is hotter than the user is comfortable with. In another example, an individual may lose their appetite for food because they are traveling, crossing time zones or experiencing jetlag. Other examples for an individual experiencing a loss in appetite may include, a busy schedule, a changing lifestyle (e.g., moving from one home environment to another), side effects due to medication, mental health conditions, or other illnesses that the individual may not be aware of.

Typically, individuals may struggle with diets or other significant alterations of an individual's nutritional intake due to a lack of palatable options. Accordingly, it may be advantageous to increase a number of palatable options for an individual by providing food options that are determined to be correlated with positive memory association of the individual, thereby increasing the individual's appetite and the likelihood that the individual will receive critical nutrients to support normal physical and cognitive functions.

Embodiments of the present invention provide methods, systems, and computer program products for analyzing user information to generate appetite improvement information. Embodiments of the present invention identify factors that correlate to a user's positive sentiment and recommend recipes for meals that are based on the identified factors.

Figure 1:
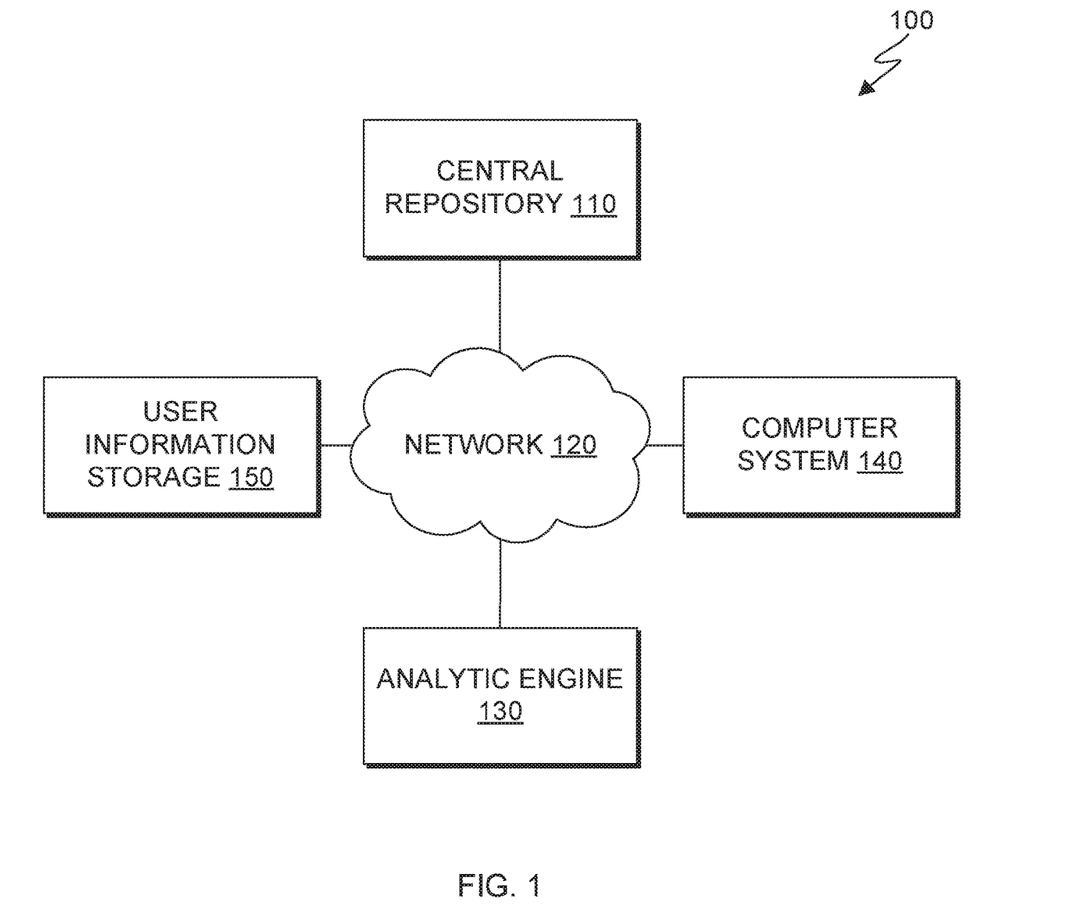
FIG. 1 is a block diagram of an appetite improvement system, in accordance with an embodiment of the present invention.

FIG. 1 is a block diagram of appetite improvement system 100, in accordance with an embodiment of the present invention. Appetite improvement system 100 includes central repository 110, analytic engine 130, computer system 140, and user information storage 150, interconnected by network 120. In this embodiment, central repository 110, analytic engine 130 and user information storage 150 of appetite improvement system 100 are each a part of separate computing systems connected by network 120. In another embodiment, a portion of such components may be arranged in one or more computing systems, such that any separate component is configured to exchange data between one another over network 120. Furthermore, such computing systems, including computer system 140, may be desktop computers, laptop computers, specialized computer servers, or any other computer system known in the art. In certain embodiments, the computing systems may represent computer systems utilizing clustered computers and components to act as a single pool of seamless resources when accessed through network 120. For example, such embodiments may be used in data center, cloud computing, storage area network (SAN), wide area network (WAN), and network attached storage (NAS) applications. In certain embodiments, the computing systems described herein represent virtual machines. In general, the computing systems described herein are representative of any electronic device, or combination of electronic devices, capable of executing machine-readable program instructions, in accordance with an embodiment of the present invention, as described in greater detail with regard to FIG. 5. In this embodiment, the computing systems are implemented in various cloud computing environments, as described in greater detail with regard to FIGS. 6 and 7.

Network 120 can be, for example, a local area network (LAN), a wide area network (WAN) such as the Internet, or a combination of the two, and include wired, wireless, or fiber optic connections. In general, network 120 can be any combination of connections and protocols that will support communications between central repository 110, analytic engine 130, computer system 140, and user information storage 150, in accordance with an embodiment of the invention.

Figure 2:
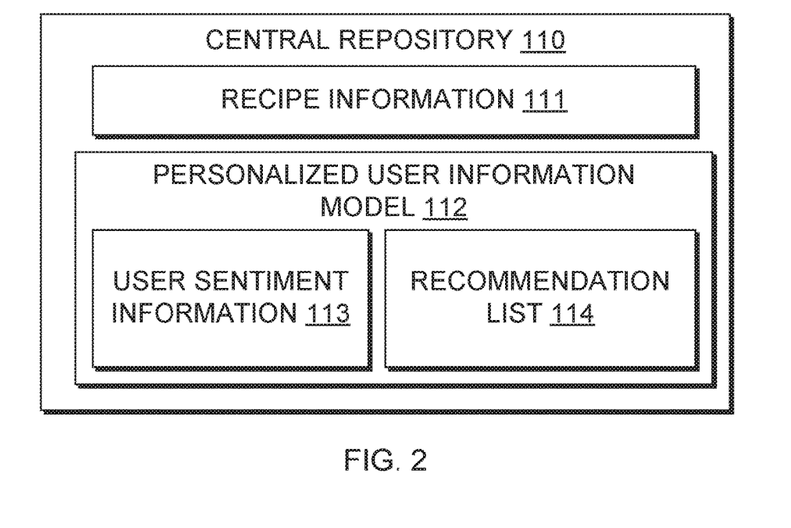
FIG. 2 is a block diagram of appetite improvement information stored in a central repository for the appetite improvement system, in accordance with an embodiment of the present invention.

Central repository 110 represents a storage component configured to store appetite improvement information generated from analytic engine 130 based on user information received from user information storage 150, as described in greater detail with regard to FIG. 2. In this embodiment, central repository 110 includes one or more data structures, tables or databases, such as a relational database for storing appetite improvement information. Appetite improvement information may be generated and populated in central repository 110 in real-time (i.e., as user information is updated and/or collected), in incremental, and/or batch operations.

Analytic engine 130 is a software component configured to process and analyze user information stored in user information storage 150 and generate appetite improvement information for storage in central repository 110. In one embodiment, analytic engine 130 may be a software component that is part of a multi-modal electroencephalogram data-collection and adaptive signal processing system configured to handle single or multi-user brainwave applications. For example, analytic engine 130 may have access to a table that identifies predefined characteristics of brain state that are associated with a positive user sentiment. In this example, analytic engine 130 may implement various analysis tools to interpret user behavior based on the user's monitored brain state, and determine whether the user's monitored brain state matches any of the predefined characteristics associated with a positive user sentiment.

In one embodiment, analytic engine 130 may be configured with other content analysis tools, such as a semantic analyzer, or a sentiment analyzer. For example, analytic engine 130 may include a web crawler to access social media information stored in, or operatively connected to (i.e., fed to), user information storage 150. In this example, analytic engine 130 may identify information that interests a user, by accessing web pages and other text content that the user shares, reposts, etc. Furthermore, analytic engine 130 may apply a weighting and/or ranking mechanism to identify which information that is the most interest to the user by determining the frequency of occurrences for the shares and/or reposts, or by using natural language processing to understand the tone and sentiment of the user (e.g., level of excitement, enthusiasm, etc.) for the shares and/or reposts. Accordingly, the information that is identified as the most interest to the user may be further processed and analyzed to identify factors of the information that correlate to a positive users sentiment, where the factors may include themes, subjects, objects, people, hobbies, activities, etc.

Computer system 140 represents a computing platform configured to monitor a user health information, and other physical interactions the user performs. As previously described, computer system 140 may be a desktop computer, laptop computer, specialized computer server, or any other computer system known in the art. In one embodiment, computer system 140 may be part of a configured to capture a user's facial expression in order to determine a correlation between the user's sentiment and any food that the user comes into interaction with. In another embodiment, computer system 140 may be part of a multi-modal electroencephalogram data-collection and adaptive signal processing system, where computer system 140 may include a headset or another sensor device configured to collect brain state information of a user. In yet another embodiment, computer system 140 may be representative of a device that is configured to monitor real-time biometric data, such as a heartrate, blood pressure, etc.

Figure 3:
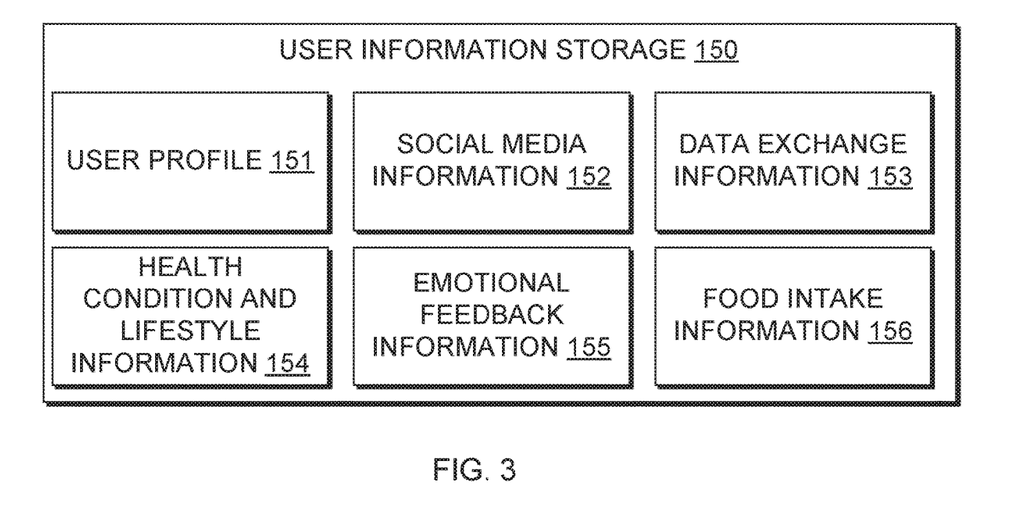
FIG. 3 is a block diagram of user information collected and stored in a user information storage for the appetite improvement system, in accordance with an embodiment of the present invention.

User information storage 150 represents a computing platform that stores, or has access to, a plurality of data received from various data sources, as described in greater detail with regard to FIG. 3. In one embodiment, user information storage 150 may be collected and filtered by analytic engine 130. For example, analytic engine 130 may access various data sources through user information storage 150 to obtain personal details of a user, social media interactions of a user, exchanges in emails/text messages/instant messages involving a user, health information of a user, schedule and other lifestyle information of the user, emotional feedback information (e.g., brain state data) of the user, and food intake information of the user. In this example, analytic engine 130 processes the user information to identify factors which correlate to a positive user sentiment. Analytic engine 130 may determine that user-posted images that include the user smiling may constitute as a positive user sentiment. Accordingly, analytic engine 130 may perform image analysis on images that include the user smiling to identify factors which may correlate to the positive user sentiment. In another instance, analytic engine 130 may process the user's personal schedule to identify possible activities that the user frequently participates in. For example, if analytic engine 130 identifies that the user frequently participates in rock climbing, then analytic engine 130 may flag rock climbing as a possible correlation to positive user sentiment.

The descriptions of the various embodiments of the present invention have been presented for the purposes of illustration, but are not intended to be exhaustive or limited to the embodiments disclosed. Many modifications and variations will be apparent to those of ordinary skill in the art without departing form the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

FIG. 2 is a block diagram of appetite improvement information stored in central repository 110 for appetite improvement system 100, in accordance with an embodiment of the present invention. In this embodiment, central repository 110 stores appetite improvement information including, recipe information 111 and personalized user information model 112.

Recipe information 111 represents a collection of information identifying recipes, their corresponding nutritional information (e.g., fat percent, amount of sugar, amount of protein, etc.) and corresponding properties (e.g., shape, color, taste, etc.). For example, an entry in a table of recipe information 111 may identify a food item, such as a peanut butter and jelly sandwich. In this example, the recipe for a peanut butter and jelly sandwich is stored in recipe information 111 as well as the corresponding nutritional information. Furthermore, properties of the peanut butter and jelly sandwich may also be maintained, such as relative levels of sweetness, bitterness, sourness, saltiness, and umami, as well as possible shapes (e.g., square, triangle, etc.), textures (e.g., soft, crunchy, etc.), and colors. In one embodiment, recipe information 111 is populated automatically, by applying natural language processing, semantic analysis, and other rule-based and machine learning techniques to a corpus of recipe, nutrition, and food property information. In another embodiment recipe information 111 may be modified by an administrative user of central repository 110. In one example, analytic engine 130 may use information stored relational databases of recipe information 111 to provide comprehensive profiles for various food items. For example, analytic engine 130 may provide a profile for apple pie, indicating that it is a sweet, golden-brown, round food item with a specific nutritional profile corresponding to a specific recipe.

Personalized user information model 112 represents a collection of information, correlations, and models generated by analytic engine 130 based on user information stored in user information storage 150. In this embodiment, personalized user information model 112 includes user sentiment information 113 and recommendation list 114. User sentiment information 113 represents information correlating a user's sentiment with food, properties of the food, and other factors (e.g., time of day, weather, settings, etc.).

Recommendation list 114 represents a list of recipes (i.e., steps to prepare food) that is generated by analytic engine 130.

In an example embodiment, analytic engine 130 may process and analyze user information from user information storage 150 to generate user sentiment information 113. In another example embodiment, user sentiment information 113 may represent information used to identify various factors such as settings, objects, environmental conditions, hobbies, activities, times of day, and/or other factors that correlate to either a positive or negative user sentiment. If analytic engine 130 determines that a particular factor correlates with a positive user sentiment, then analytic engine 130 may identify the particular factor as a positive token and store the positive token in user sentiment information 113. In another example embodiment, analytic engine 130 may rank factors based on a strength of the correlation to a positive user sentiment, and if the strength of the correlations are above a specified threshold, then analytic engine 130 stores those factors with the high strength correlations as positive tokens.

In one example, analytic engine 130 may determine that if a user expresses a smile or other type of facial expression, then analytic engine 130 may correlate the smile or other type of facial expression to a positive user sentiment. Furthermore, information for the expressed smile or the other type of facial expression will be stored along with its determined sentiment correlation in user sentiment information 113. In another example, analytic engine 130 may determine that if a user responds to an email in an enthusiastic or positive tone, then analytic engine 130 may correlate phrases, expressions or words identified in the email to a positive user sentiment. In another example, a community gardening club may update their website with an award congratulating a particular user with the best gardener award. In this update, the community gardening club may include images that include the particular user smiling next to their prized garden. Accordingly, analytic engine 130 may analyze the images of the particular user to determine that the particular user is expressing a positive sentiment and further identify aspects of the image that are associated with the positive sentiment, such as flowers. In general, analytic engine 130 may perform image analysis, text analysis, natural language processing, semantic and sentiment analysis, as well as other types of rule-based and machine learning techniques to determine which factors correlate with either a positive or negative user sentiment and store this information in user sentiment information 113.

Recommendation list 114 represents a list of recipes and other details (e.g., preparation techniques, times of day to prepare the recipe, substitution ingredients, customized preferences, etc.) that is generated by analytic engine 130 based on processing and analyzing user sentiment information 113 and recipe information 111. In this embodiment, entries of recipes in recommendation list 114 are continuously updated based on changing user information stored in user information storage 150 and appetite improvement information stored in central repository 110. For example, if a flower is determined to a positive token correlating to a user's positive sentiment, then recommendation list 114 may include food items that are prepared to resemble a flower. In another example, if analytic engine 130 determines that a user is enthusiastic about a sport team based on text analysis, then recommendation list 114 may include food items that are prepared to include themes of the sports team (e.g., colors, visualizations, etc.).

FIG. 3 is a block diagram of user information stored in user information storage 150 for appetite improvement system 100, in accordance with an embodiment of the present invention. User profile 151 represents data describing a user's age, gender, job profession, and other personal details (e.g., geolocation). Social media information 152 represents a collection of information related to social media interactions. For example, social media information 152 may include blog posts, status updates, images, online profile information (e.g., activities, hobbies, etc.), frequently visited or checked-in locations, comments, and other information collected from various social media sources. Data exchange information 153 represents a collection of information related to other interactions performed on their personal device (e.g., computer system 140). For example, text content, images, metadata, and other information extracted from exchanges involving text messages, emails, instant messages, and other computer-to-computer interactions may be included in data exchange information 153.

Health condition and lifestyle information 154 represents a collection of information related to a user's physical health and any pertinent lifestyle information. For example, biometric data (e.g., a heart rate) may be collected by computer system 140 and stored in health condition and lifestyle information 154. Pertinent health condition and lifestyle information 154 may include information describing any major life event change (e.g., lost friends or family members, moved to a nursing home, etc.), weather changes (e.g., the weather is getting too hot), work schedules, stressful environments, and/or other personal related matters.

Emotional feedback information 155 represents a collection of information related to a user's emotional health. For example, computer system 140 may be part of an EEP system that can monitor brain state data and determine a user's emotional state (e.g., feelings, emotions, conditions, etc.). Food intake information 156 represents a collection of information related to a user's eating habits. For example, computer system 140 may be configured to monitor and evaluate whether the user has reduced their food intake recently (e.g., whether a user eats less often or whether a user's food intake is getting less comparing to before).

In general, user information stored in user information storage 150 may be continuously updated based on the updates received by the corresponding information sources, and based on information monitored by computer system 140. For example, computer system 140 may monitor brain state data while a user eats a particular food item, and accordingly store the brain state data and identify the data as being associated with the particular food item. In another example, computer system 140 may capture a user's facial expression in real-time while the user eats a particular food item, and accordingly store the facial expression information and identify the information as being associated with the particular food item.

Figure 4:
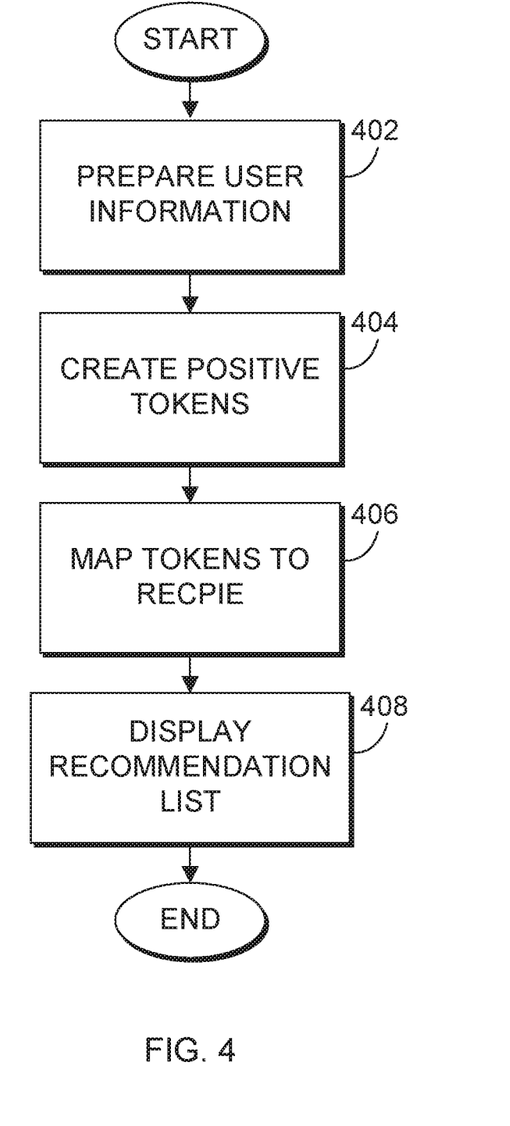
FIG. 4 is a flowchart illustrating operational steps for creating and storing enrichment analysis data, in accordance with an embodiment of the present invention.

FIG. 4 is a flowchart illustrating operational steps for generating appetite improvement information, in accordance with an embodiment of the present invention. In this embodiment, the appetite improvement information includes user sentiment information 113 as well as recommendation list 114.

Analytic engine 130 prepares the user information (step 402). In one embodiment, analytic engine 130 may evaluate, validate, curate, transform and/or enhance the user information included in user information storage 150 prior to analyzing. Furthermore, analytic engine 130 may rely on rule-based and/or machine learning techniques to ensure that all relevant images, text information, audio files and metadata are in a usable format prior to analyzation. After the user information is prepared, analytic engine 130 generates positive tokens based on the user information (step 404). For example, analytic engine 130 may apply various analysis tools and reference predefined definitions of user sentiment, to determine which factors of the user information correlate with a positive user sentiment, as described above. Furthermore, analytic engine 130 ranks the correlations to the positive user sentiment, based on the strength of the correlation, and the highest ranking correlations are generated into positive tokens used in subsequent processing. In instances where user information updates are received, analytic engine 130 may also analyze and process the user information included in the corpus updates to create, generate or regenerate, positive tokens.

Once positive tokens are stored in user sentiment information 113, analytic engine 130 maps, or applies, the positive tokens to recipes stored in recipe information 111 (step 406). For example, analytic engine 130 may search recipes stored in recipe information 111 to identify food options that match, can be modified to match, include, or incorporate, the positive tokens stored in user sentiment information 113. In one example, a positive token for a user may be a baseball, and accordingly, analytic engine 130 identifies recipes in recipe information 111 that can be modified to incorporate a baseball theme, or be prepared such that the final food product is in the shape and resembles a baseball. Accordingly, any identified recipes are included in recommendation list 114 and subsequently displayed to the user (step 408).

Figure 5:
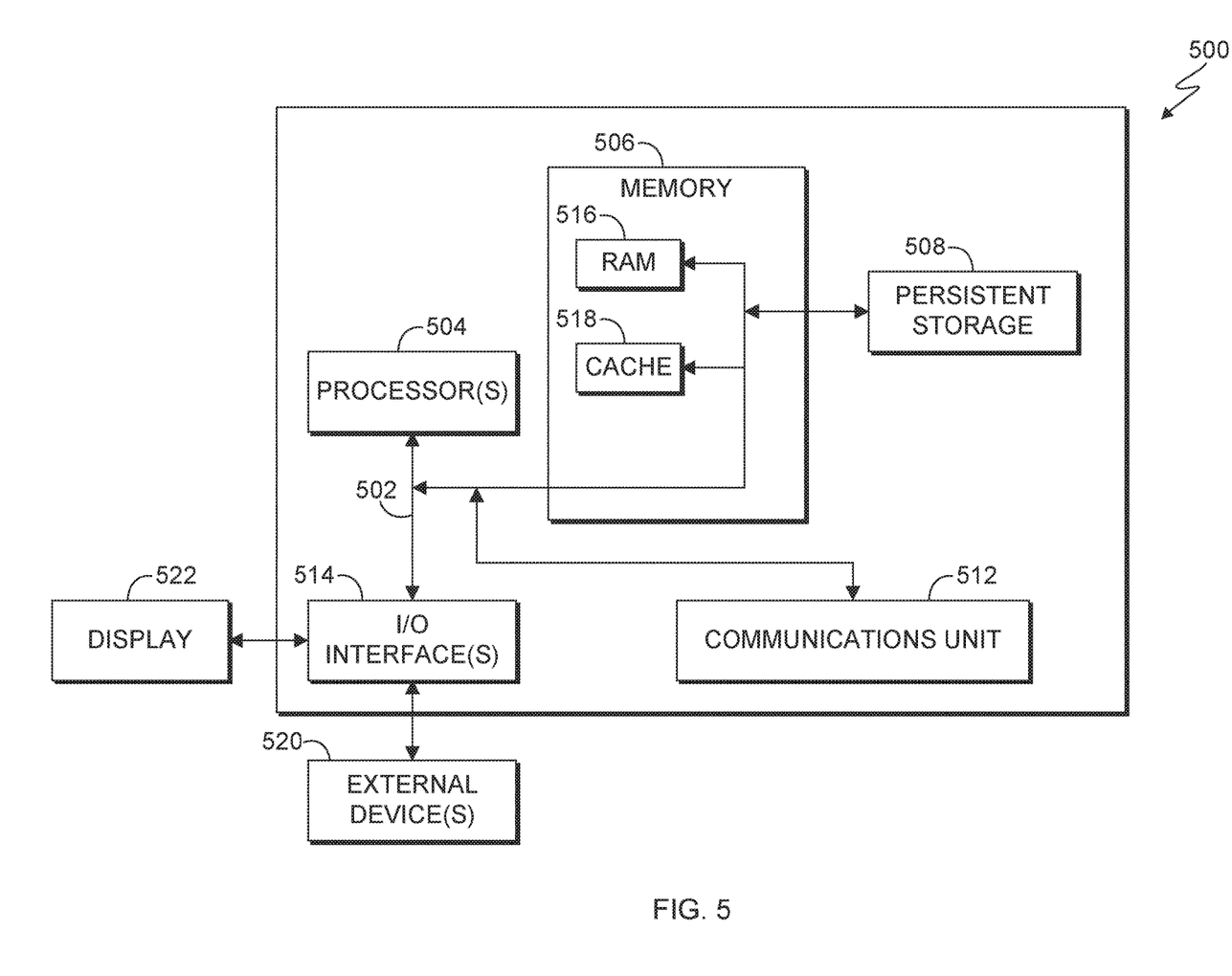
FIG. 5 is a block diagram of internal and external components of the computer systems of FIG. 1, in accordance with an embodiment of the present invention.

FIG. 5 is a block diagram of internal and external components of a computer system 500, which is representative the computer systems of FIG. 1, in accordance with an embodiment of the present invention. It should be appreciated that FIG. 5 provides only an illustration of one implementation and does not imply any limitations with regard to the environments in which different embodiments may be implemented. In general, the components illustrated in FIG. 5 are representative of any electronic device capable of executing machine-readable program instructions. Examples of computer systems, environments, and/or configurations that may be represented by the components illustrated in FIG. 5 include, but are not limited to, personal computer systems, server computer systems, thin clients, thick clients, laptop computer systems, tablet computer systems, cellular telephones (e.g., smart phones), multiprocessor systems, microprocessor-based systems, network PCs, minicomputer systems, mainframe computer systems, and distributed cognitive computing environments that include any of the above systems or devices.

Computer system 500 includes communications fabric 502, which provides for communications between one or more processors 504, memory 506, persistent storage 508, communications unit 512, and one or more input/output (I/O) interfaces 514. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses.

Memory 506 and persistent storage 508 are computer-readable storage media. In this embodiment, memory 506 includes random access memory (RAM) 516 and cache memory 518. In general, memory 506 can include any suitable volatile or non-volatile computer-readable storage media. Software is stored in persistent storage 508 for execution and/or access by one or more of the respective processors 504 via one or more memories of memory 506.

Persistent storage 508 may include, for example, a plurality of magnetic hard disk drives. Alternatively, or in addition to magnetic hard disk drives, persistent storage 508 can include one or more solid state hard drives, semiconductor storage devices, read-only memories (ROM), erasable programmable read-only memories (EPROM), flash memories, or any other computer-readable storage media that is capable of storing program instructions or digital information.

The media used by persistent storage 508 can also be removable. For example, a removable hard drive can be used for persistent storage 508. Other examples include optical and magnetic disks, thumb drives, and smart cards that are inserted into a drive for transfer onto another computer-readable storage medium that is also part of persistent storage 508.

Communications unit 512 provides for communications with other computer systems or devices via a network (e.g., network 120). In this exemplary embodiment, communications unit 512 includes network adapters or interfaces such as a TCP/IP adapter cards, wireless Wi-Fi interface cards, or 3G or 4G wireless interface cards or other wired or wireless communication links. The network can comprise, for example, copper wires, optical fibers, wireless transmission, routers, firewalls, switches, gateway computers and/or edge servers. Software and data used to practice embodiments of the present invention can be downloaded through communications unit 512 (e.g., via the Internet, a local area network or other wide area network). From communications unit 512, the software and data can be loaded onto persistent storage 508.

One or more I/O interfaces 514 allow for input and output of data with other devices that may be connected to computer system 500. For example, I/O interface 514 can provide a connection to one or more external devices 520, such as a keyboard, computer mouse, touch screen, virtual keyboard, touch pad, pointing device, or other human interface devices. External devices 520 can also include portable computer-readable storage media such as, for example, thumb drives, portable optical or magnetic disks, and memory cards. I/O interface 514 also connects to display 522.

Display 522 provides a mechanism to display data to a user and can be, for example, a computer monitor. Display 522 can also be an incorporated display and may function as a touch screen, such as a built-in display of a tablet computer.

Figure 6:
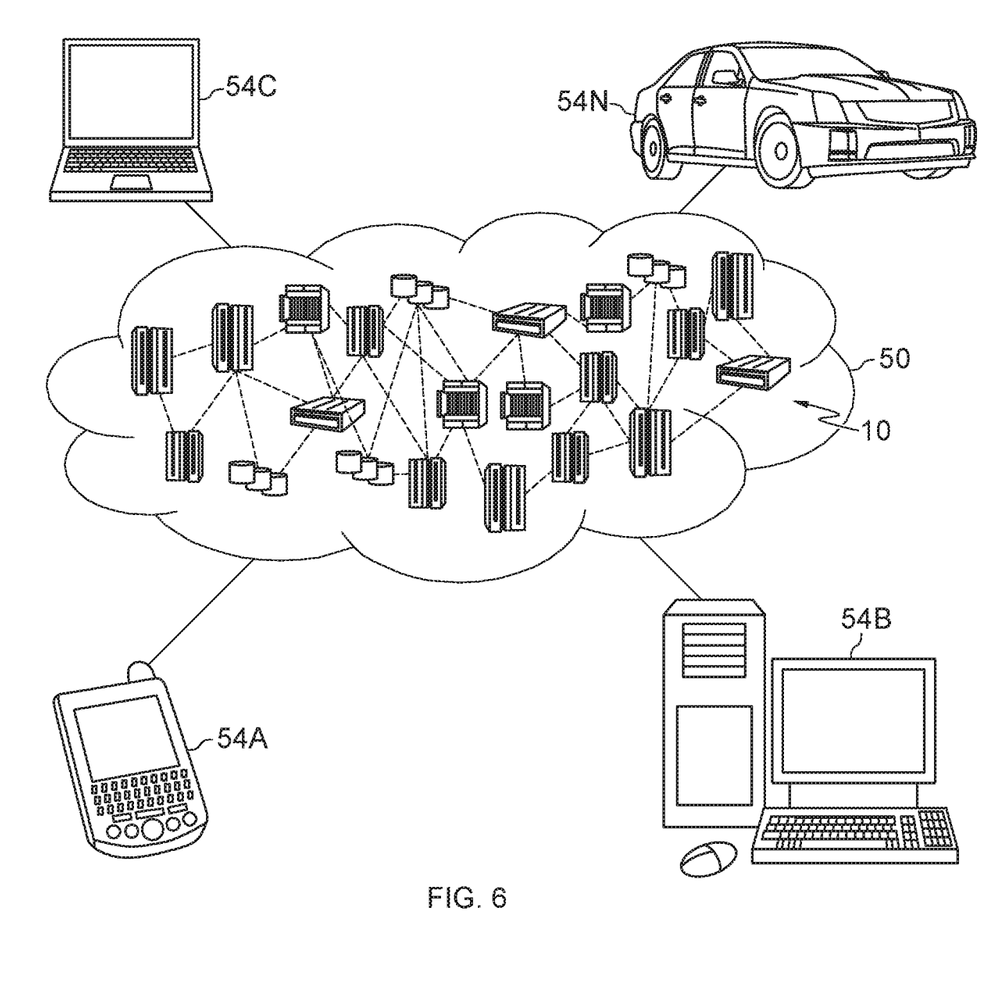
FIG. 6 depicts a cloud computing environment, in accordance with an embodiment of the present invention.

Referring now to FIG. 6, illustrative cognitive computing environment 50 is depicted. As shown, cognitive computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cognitive computing environment 50 to offer infrastructure, platforms and/or software as services for which a cloud consumer does not need to maintain resources on a local computing device. The types of computing devices 54A-N shown in FIG. 5 are intended to be illustrative only and that cloud computing nodes 10 and cognitive computing environment 50 can communicate with any type of computerized device over any type of network and/or network addressable connection (e.g., using a web browser).

Figure 7:
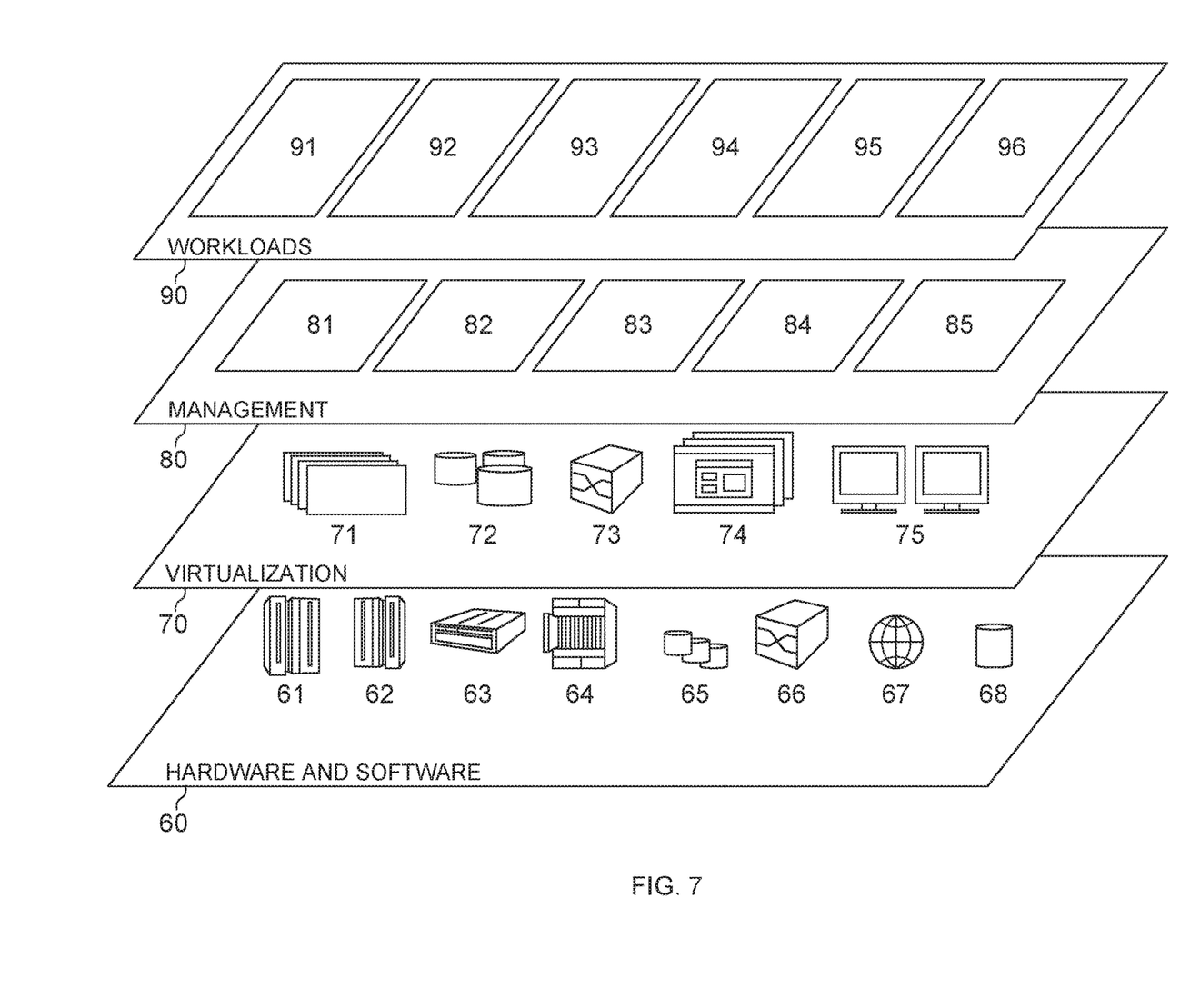
FIG. 7 depicts abstraction model layers, in accordance with an embodiment of the present invention.

Referring now to FIG. 7, a set of functional abstraction layers provided by cognitive computing environment 50 (FIG. 6) is shown. The components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cognitive computing environment. Metering and Pricing 82 provide cost tracking as resources are utilized within the cognitive computing environment, and billing or invoicing for consumption of these resources. In one example, these resources may comprise application software licenses. Security provides identity verification for cloud consumers and tasks, as well as protection for data and other resources. User portal 83 provides access to the cognitive computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cognitive computing environment may be utilized. Examples of workloads and functions which may be provided from this layer include: mapping and navigation 91; software development and lifecycle management 92; virtual classroom education delivery 93; data analytics processing 94; transaction processing 95; and appetite improvement system 96.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cognitive computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cognitive computing environment is service oriented with a focus on statelessness, low coupling, modularity, and semantic interoperability. At the heart of cloud computing is an infrastructure comprising a network of interconnected nodes.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
   analyzing, by one or more computer processors, a plurality of user information sources related to a user;
   defining, by the one or more computer processors, a positive user sentiment expressed by the user in the plurality of user information sources;
   identifying, by the one or more computer processors, at least one factor that correlates with the positive user sentiment expressed by the user;
   ranking, by the one or more computer processors, the at least one factor based on a strength of the correlation;
   responsive to determining that the strength of the correlation is above a predefined threshold, storing, by the one or more computer processors, the at least one factor as a positive token;
   generating, by the one or more computer processors, a plurality of food profiles, wherein a respective food item in the plurality of food profiles includes a corresponding recipe information, a corresponding nutritional information, and a corresponding food property information;
   responsive to mapping the at least one positive token to the plurality of food profiles, identifying, by the one or more computer processors, based on the corresponding recipe information, the corresponding nutritional information, and the corresponding food property information, at least one food item that incorporates the at least one positive token, wherein the at least one positive token is associated with the positive sentiment expressed by the user; and
   continuously updating, by the one or more computer processors, a recommendation list including the at least one food item having a preparation information to resemble the at least one positive token to the user.

2. The method of claim 1, further comprising:
   receiving, by the one or more computer processors, at least one image related to the user;
   defining, by the one or more computer processors, the positive user sentiment with respect to the at least one image based on machine learning techniques; and
   applying, by the one or more computer processors, image analysis on the at least one image to identify the at least one factor that correlates with the positive user sentiment.

3. The method of claim 1, further comprising:
   receiving, by the one or more computer processors, a brain state data related to the user;
   defining, by the one or more computer processors, the positive user sentiment with respect to the brain state data based on machine learning techniques; and
   applying, by the one or more computer processors, an analysis on the brain state data to identify the at least one factor that correlates with the positive user sentiment.

4. The method of claim 1, wherein the at least one factor that correlates with the positive user sentiment is selected from the group consisting of:
   a theme, a subject, an object, a person, an activity, a setting, an environmental condition, and a time of day.

5. The method of claim 3, further comprising:
   monitoring, by the one or more computer processors, the brain state data while the user eats a particular food item; and
   storing, by the one or more computer processors, the brain state data as being associated with the particular food item.

6. The method of claim 1, wherein analyzing the plurality of user information sources related to the user is selected from the group consisting of:
   performing image analysis, performing text analysis, performing natural language processing, performing semantic analysis, performing sentiment analysis, performing rule-based analysis, and performing machine learning-based analysis.

7. The method of claim 1, further comprising:
   responsive to determining that no food item is identified to incorporate the at least one positive token, modifying, by the one or more computer processors, the at least one food item to incorporate the at least one positive token.

* * * * *